United States Patent [19]

Serizawa et al.

[11] Patent Number: 5,656,939
[45] Date of Patent: Aug. 12, 1997

[54] APPARATUS FOR MEASURING HARDNESS OF ULTRAVIOLET CURING TRANSFORMATION AGENT COMPRISING STAIN AND METHOD FOR THE SAME

[75] Inventors: Izumi Serizawa; Masahiro Kurano, both of Chofu; Yasusuke Takahashi, Funabashi, all of Japan

[73] Assignee: ORC Manufacturing Co., Ltd., Tokyo, Japan

[21] Appl. No.: 452,599

[22] Filed: May 25, 1995

[30] Foreign Application Priority Data

Feb. 28, 1995 [JP] Japan ................................. 7-040507

[51] Int. Cl.$^6$ ..................................................... G01G 7/10
[52] U.S. Cl. ................................. 324/713; 73/78
[58] Field of Search ........................ 73/78, 150 R; 324/693, 702, 713

[56] References Cited

U.S. PATENT DOCUMENTS

4,715,007 12/1987 Fujita et al. ..................... 73/150 R

*Primary Examiner*—Robert Raevis
*Attorney, Agent, or Firm*—Longacre & White

[57] ABSTRACT

An apparatus for measuring hardness of an ultraviolet curing transformation agent comprising a stain of the present invention comprises a light source device for emitting beams including ultraviolet rays, an optical filter member through which the ultraviolet rays having a predetermined wavelength among the beams emitted from the light source device pass, and a measuring device for measuring electric conductivity of the ultraviolet curing transformation agent comprising the stain, provided at a location where the ultraviolet rays having the predetermined wavelength irradiate. Further, the measuring device comprises an electrode portion including electrodes on which the ultraviolet curing transformation agent is applied, and the electrodes are connected through a power supply and a measuring device for measuring the electric conductivity. Therefore, the measuring apparatus of the present invention can readily and rapidly determine the hardness of the UV curing transformation agent comprising a stain such as a pigment, corresponding to the printing condition.

14 Claims, 9 Drawing Sheets

APPARATUS FOR MEASURING HARDNESS OF ULTRAVIOLET CURING TRANSFORMATION AGENT COMPRISING STAIN AND METHOD FOR THE SAME

BACKGROUND OF THE INVENTION

1. FIELD OF THE INVENTION

The present invention relates to an apparatus and a method for measuring hardness of an ultraviolet curing transformation agent comprising a stain which is applied on a work and dried with an optical device.

2. PRIOR ART

Ultraviolet curing transformation agents have been widely used because they can be applied to un-heat-treatable materials and enable high-speed printing. The ultraviolet curing transformation agents are now utilized in various industrial fields, for example, general printed matter, compact discs, building materials, floor materials such as tiles, wall materials, resist for printed board, beverage cans and so on.

After printed on a material, the ultraviolet (UV) curing transformation agent is dried by a conveyor apparatus comprising an ultraviolet ray source such as a high-pressure mercury-vapor lamp or a metal halide lamp while the printing material is transferred. Alternatively, the UV curing transformation agent is dried by an apparatus comprising a light source for spotlighting. The most significant point for the use of the transformation agents is adjusting the intensity of ultraviolet ray and the ultraviolet ray radiation time for curing (drying) the transformation agent in accordance with the types of transformation agents.

Various means for measuring the hardness of the ultraviolet curing transformation agents have been proposed. For example, the hardness is measured by a taping test, a cross-cutting test a dye immersing method, or examined by visual examination, tactile impression and so on.

Further, in order to measure the precise hardness, there are nuclear magnetic resonance (NMR), infrared spectrophotometry, and a method for measuring the extension of transformation agents, but actually these are employed only in researches.

Furthermore, there has been proposed a method for determining the hardness from the change in electric resistance or the transformation agent as a method for measuring the hardness of the transparent ultraviolet curing transformation agent. The apparatus for carrying out this method comprises a light source device, and electrodes provided at both sides of the ultraviolet curing transformation agent applied on an insulator and connected each other through a power supply and a measuring device for measuring the electric conductivity.

Accordingly, as the transformation agent is gradually cured by the ultraviolet ray irradiation, the electric conductivity between both electrodes is decreased. Then, the hardness of the transformation agent can be measured by the electric conductivity measuring device. It is clear from the concurrent measurement with the use of dial gauge that the decrease of the electric conductivity is proportional to the hardness of the transformation agent. That is, the hardness (dryness) is determined by measuring how much the dial gauge is suck in the transformation agent.

However, there still exist the following problems in the above-described method for measuring the hardness of the ultraviolet curing transformation agent.

(1) Because the visual examination and tactile impression depend upon operators and some kinds of standards are never established, it is hard to prevent the inconvenient phenomenon in printing process such as crystallization and back-trapping.

(2) The NMR and the infrared spectrophotometry enable the accurate measurement; however, in view of the prompt measurement, the location of the device and the environment of the device, it is difficult to use these methods in practice.

(3) In the case of ultraviolet curing transformation agent comprising a stain, the stain absorbs the ultraviolet ray having a predetermined wavelength and the electric conductivity is kept high and not varied in accordance with the hardness of the UV curing transformation agent while the UV ray irradiates. Therefore, the determination of the hardness of the UV curing transformation agent based on the change in electric conductivity is impossible.

SUMMARY OF THE INVENTION

It is an object of the present invention to provide an apparatus and a method for measuring hardness of an ultraviolet curing transformation agent comprising a stain, which can measure the hardness of the ultraviolet curing transformation agent in accordance with the printing condition, and which can accurately and readily measure the hardness of the ultraviolet curing transformation agent comprising a stain such as a pigment.

In order to solve the above problems, an apparatus for measuring hardness of an ultraviolet curing transformation agent comprising a stain of the present invention comprises a light source device for emitting beams including ultraviolet rays, an optical filter member through which the ultraviolet rays having a predetermined wavelength among the beams emitted from the light source device pass, and a measuring device for measuring electric conductivity of the ultraviolet curing transformation agent comprising the stain, provided at a location where the ultraviolet rays having the predetermined wavelength irradiate, and the measuring device comprises an electrode portion including electrodes on which the ultraviolet curing transformation agent is applied, and the electrodes are connected through a power supply and a measuring device for measuring the electric conductivity.

The ultraviolet curing transformation agent may be applied to one of the electrodes and the electrodes are piled up, and one of the electrodes to be irradiated with the ultraviolet rays from the light source device is made of member capable of transmitting light. The electrode portion may be provided in a predetermined gas atmosphere in which oxygen is shut off.

The optical filter member may be provided at a reflector placed in an optical path of light emitted from the light source device, or provided at a condenser placed in an optical path of light emitted from the light source device, or provided at an end of a lamp of the light source device so as to interrupt an optical path of light emitted from the lamp.

A condenser may be provided at an optical path of light emitted from the light source device between the location of the optical filter member and the ultraviolet curing transformation agent. It is preferable that the optical filter member is a coherent filter of conductive multilayer films which removes light in the spectral absorption region of the stain of the ultraviolet curing transformation agent.

A method for measuring hardness of an ultraviolet curing transformation agent comprising a stain of the present invention comprises a first step of irradiating an ultraviolet curing transformation agent with light from which light in the spectral absorption region of the stain of the ultraviolet curing transformation agent is removed, and a second step of measuring electric conductivity of the ultraviolet curing transformation agent.

Alternatively, a method for measuring hardness of an ultraviolet curing transformation agent comprising a stain of the present invention comprises a first step of irradiating an ultraviolet curing transformation agent with light from which light in the spectral absorption region of the stain of the ultraviolet curing transformation agent is removed by an optical filter member, and a second step of providing the ultraviolet curing transformation agent in a predetermined gas atmosphere in which oxygen is shut off, and measuring electric conductivity of the ultraviolet curing transformation agent.

In the first step, it is preferable that light in the spectral absorption region of the stain of the ultraviolet curing transformation agent is removed by the optical filter member, and that ultraviolet rays are condensed and irradiate the ultraviolet curing transformation agent.

In the second step, it is preferable that the hardness is determined based on the decrement of the electric conductivity.

The measuring apparatus and the method of the present invention have the following effects.

(1) The ultraviolet rays having a predetermined wavelength among the beams including UV rays emitted from the light source are selectively transmitted through the optical filter and irradiate the electrode portion of the measuring device. Accordingly, the UV rays in the spectral absorption region of the stain of the UV curing transformation agent applied over the electrode are removed, which suppresses the photoelectromotive force generation.

(2) In the electrode portion, the UV curing transformation agent including the stein is applied over one of the electrodes and the electrodes are piled up, and one of the electrodes to be irradiated with light from the light source is made of member capable of transmitting light. Accordingly, the oxygen is shut off. Alternatively, the oxygen is shut off by placing the electrode portion in an atmosphere including a predetermined gas.

(3) The optical filter member is provided at the reflector, and the UV rays having the predetermined wavelength among the light emitted from the light source device are reflected by the reflector, and unnecessary beams are transmitted through the reflector. Accordingly, the photoelectromotive force is not generated in the pigment contained in the UV curing transformation agent.

(4) The optical filter member is provided at the condenser placed in the optical path of the UV rays emitted from the light source. Accordingly, when the UV rays pass through the condenser, light in the spectral absorption region of the pigment contained in the UV curing transformation agent is removed.

(5) The optical filter member is provided at the end of the lamp of the light source so as to interrupt the optical path of light from the lamp, and the optical filter member is capable of transmitting the ultraviolet ray having the predetermined wavelength to irradiate the ultraviolet curing transformation agent. Moreover, the optical filter member of the light source reflects the ultraviolet rays having a wavelength causing the photoelectromotive force in the pigment.

(6) The condenser is provided between the location of the optical filter member and 6he UV curing transformation agent, so that the UV rays having a predetermined wavelength passed through the optical filter member are condensed and irradiate the transformation agent.

(7) The conductive multilayer coherent-films are utilized as the optical filter member, so that the UV rays having a predetermined wavelength can be reflected or transmitted.

(8) As a method for measuring hardness of the UV curing transformation agent, the hardness of the UV curing transformation agent is determined by removing the UV rays in the spectral absorption region of pigment, irradiating the UV curing transformation agent with UV rays which do not cause the photoelectromotive force in the pigment, and measuring the electric conductivity of the UV curing transformation agent.

(9) The UV rays having wavelengths in the spectral absorption region of the pigment contained in the UV curing transformation agent are removed and the condensed UV rays irradiate the transformation agent, so that the photoelectromotive force is not generated in the pigment. Accordingly, the electric conductivity of the UV curing transformation agent can be measured by means of measuring instruments. If the transformation agent is placed in a predetermined gas atmosphere when the electric conductivity is measured, the anaerobic printing material can be treated.

(10) The hardness of the UV curing transformation agent is determined based on the decrement of electric conductivity, so that the UV curing transformation agent can be used in various application.

PREFERRED EMBODIMENTS OF THE PRESENT INVENTION

Preferred embodiments of the present invention will be described hereunder with reference to the accompanying drawings. In the description, the same components are represented by the same reference numerals, and the repetitive description on the same components is omitted.

Referring to FIGS. 2 to 8, the first embodiment of the present invention will be described hereunder.

Figure 1:
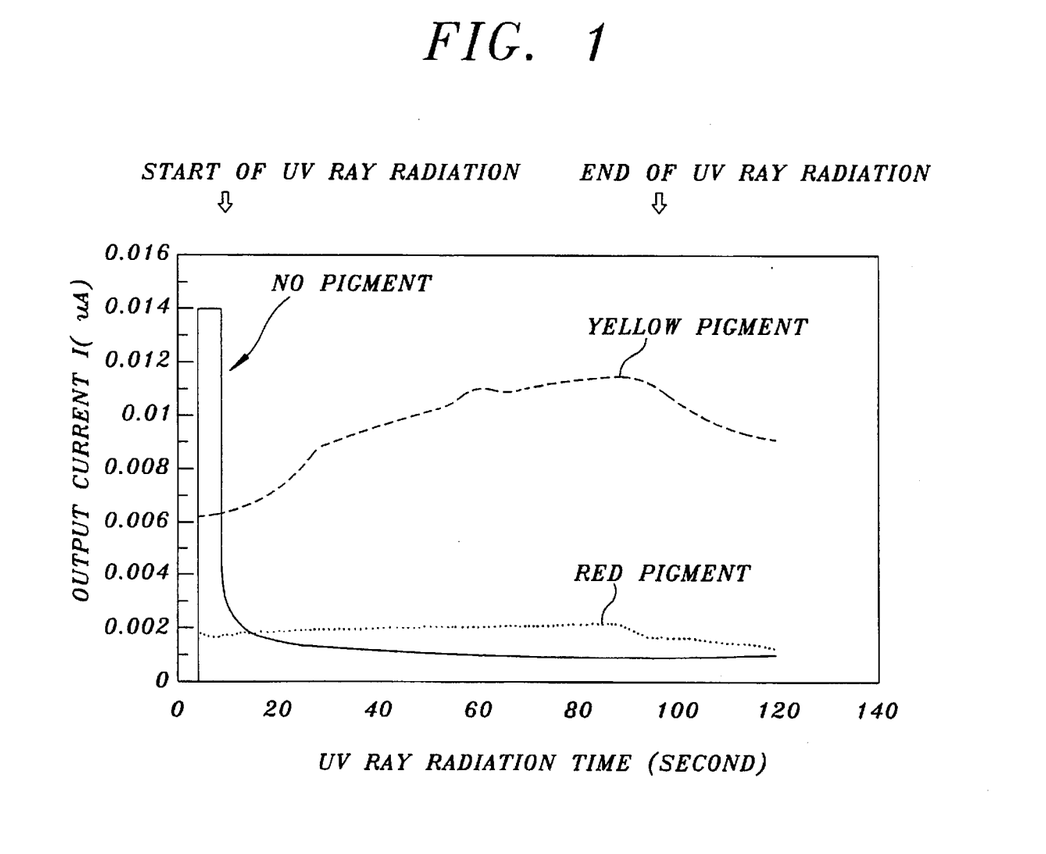
FIG. 1 is a graph showing the relationship between the ultraviolet ray radiation time and the electric conductivity, of an ultraviolet curing transformation agent comprising a pigment and an ultraviolet curing transformation agent not comprising a pigment, in accordance with the conventional method.
Figure 2:
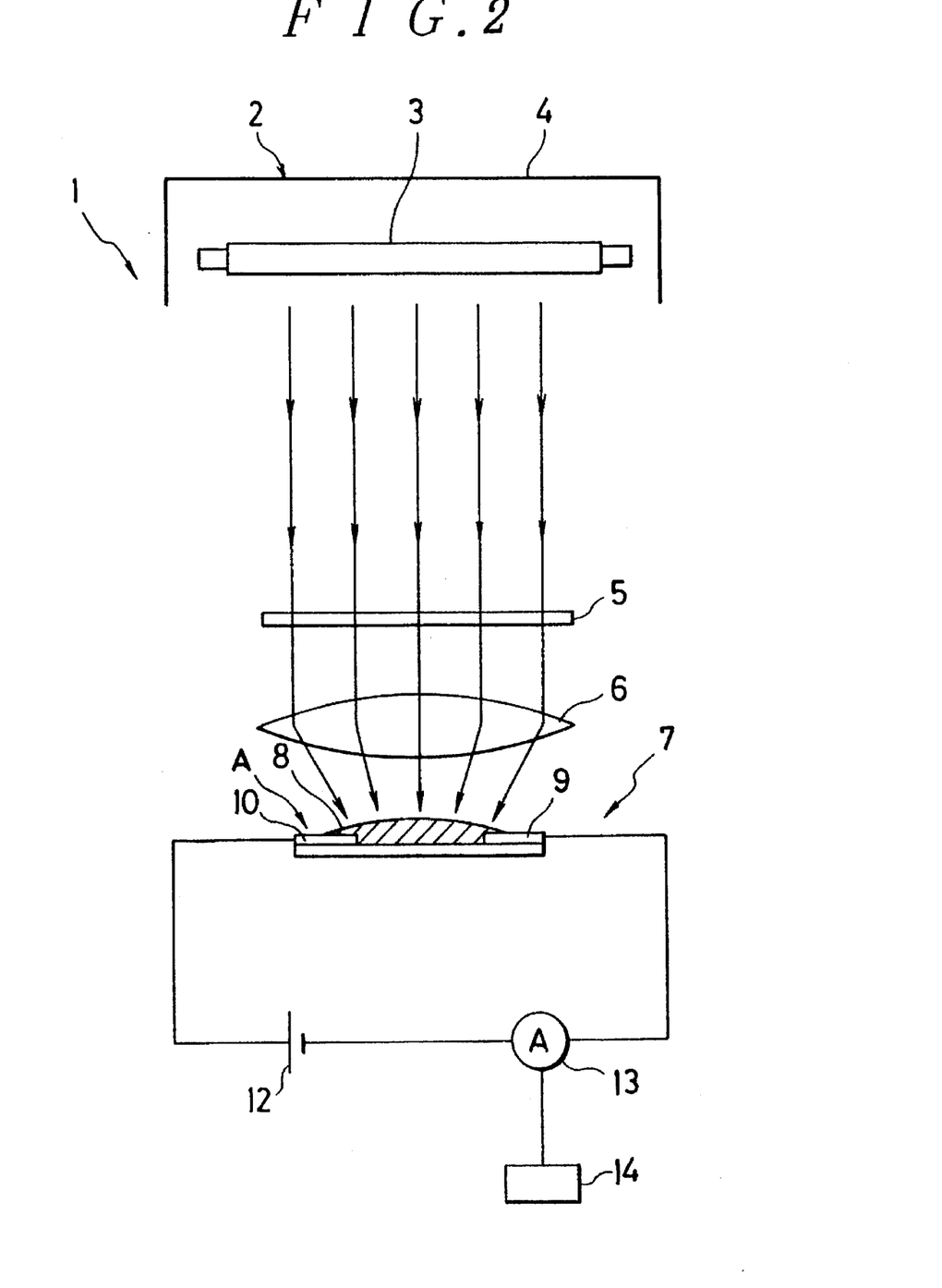
FIG. 2 is a schematic view showing a measuring apparatus according to the first embodiment of the present invention.
Figure 3:
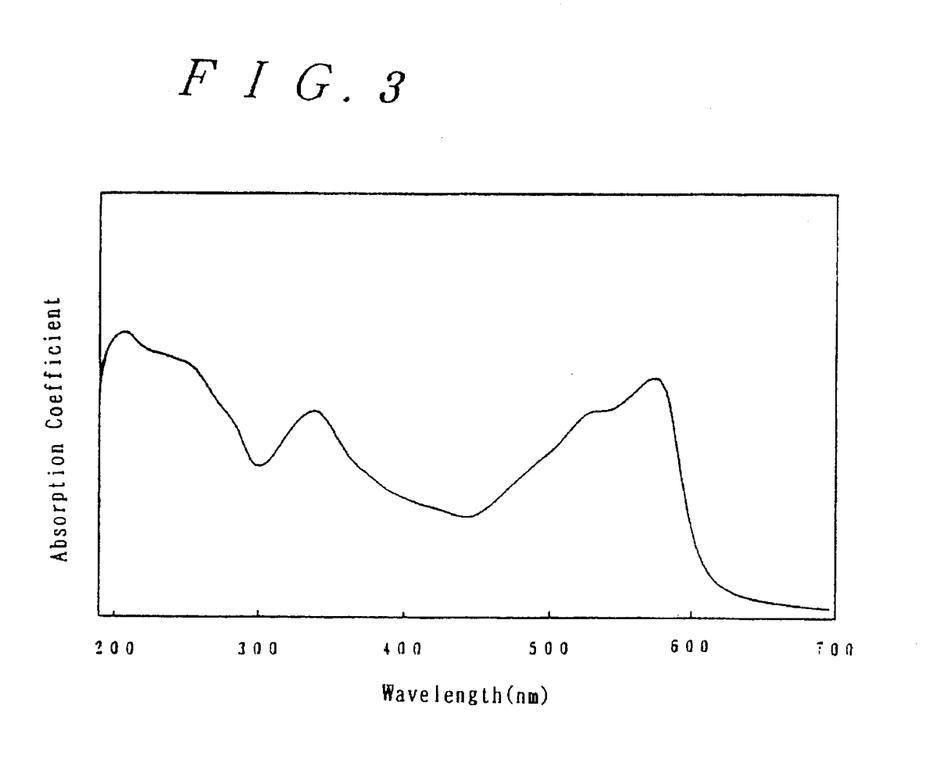
FIG. 3 is a graph showing the relationship between an absorption coefficient and an ultraviolet wavelength of the ultraviolet curing transformation agent according to the present invention.
Figure 4:
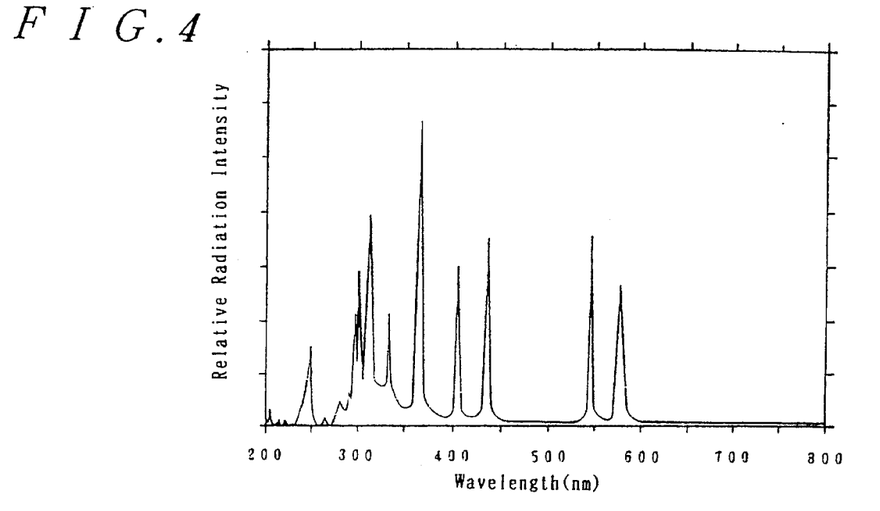
FIG. 4 is a graph showing the relationship between the relative intensity of light and the wavelength property of a mercury-vapor lamp according to the present invention.
Figure 5:
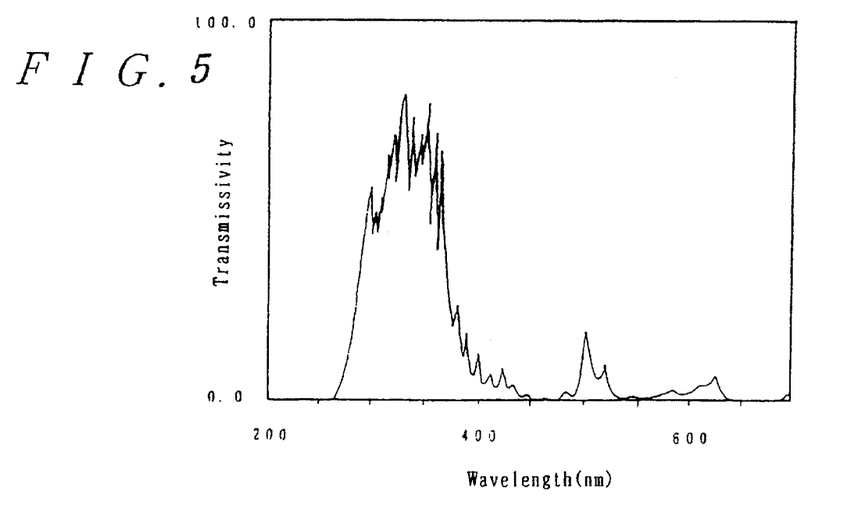
FIG. 5 is a graph showing the relationship between the transmissivity and a wavelength of ultraviolet rays passing through an optical filter member according to the present invention.
Figure 6:
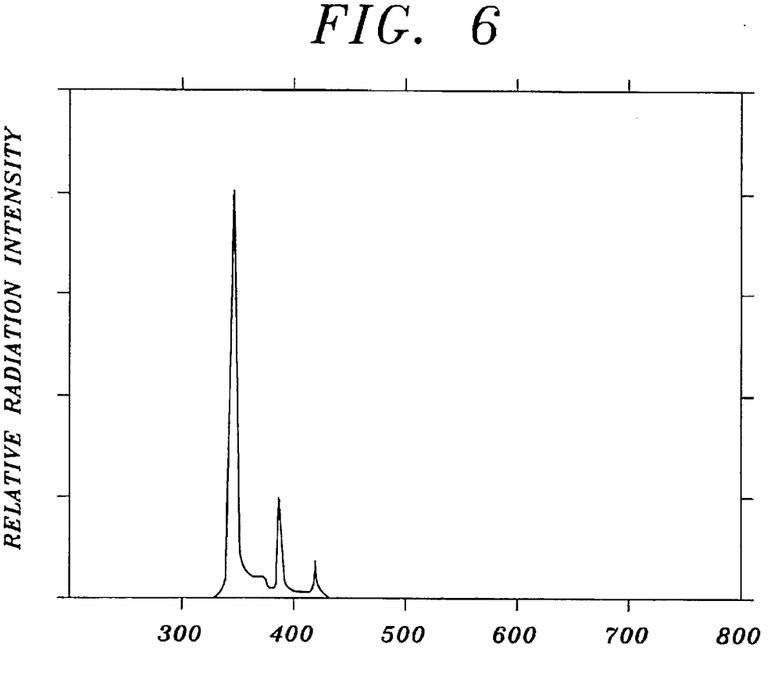
FIG. 6 is a graph showing the relationship between a wavelength of ultraviolet rays and the relative intensity of light in a case of the use of the optical filter member according to the present invention.
Figure 7:
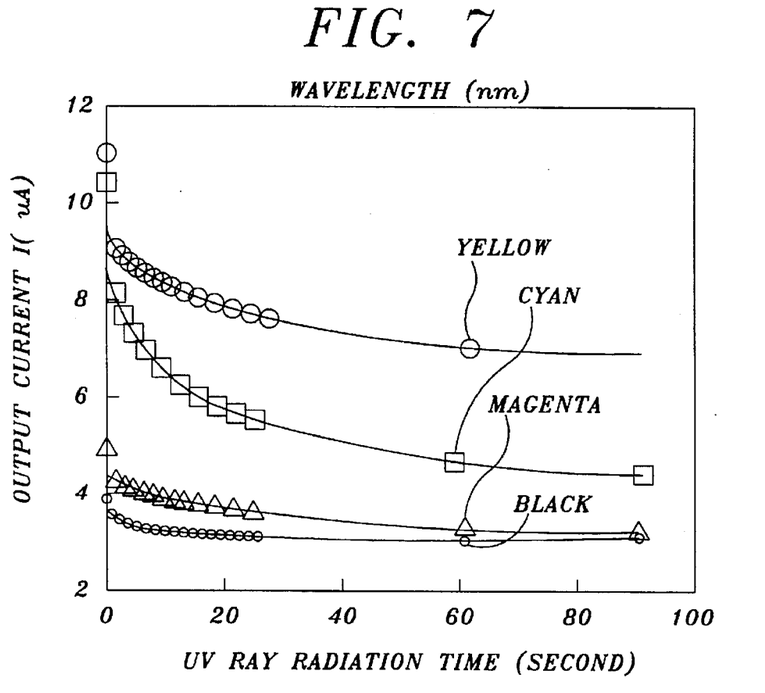
FIG. 7 is a graph showing the relationship between the ultraviolet ray radiation time and the output current, of every pigment of the ultraviolet curing transformation agent according to the present invention.
Figure 8:
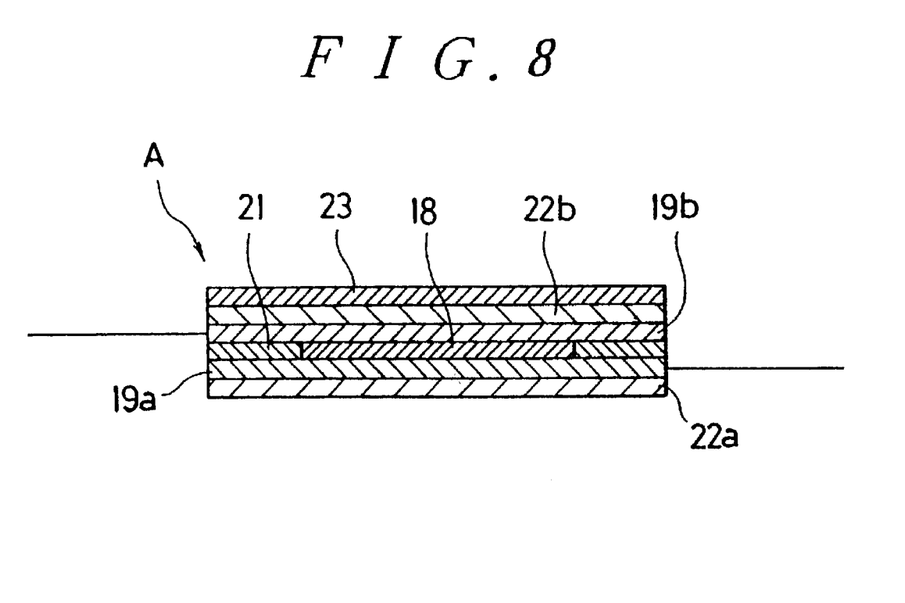
FIG. 8 is a cross-sectional view showing a modified example of electrodes according to the present invention.

FIG. 2 shows an apparatus for measuring hardness of an ultraviolet curing transformation agent; FIG. 3 shows the relationship between a wavelength of ultraviolet rays and absorption coefficients; FIG. 4 is a graph showing the relationship between a wavelength of ultraviolet rays and the relative intensity of light; FIG. 5 is a graph showing the relationship between a wavelength of ultraviolet rays and the transmissivity; FIG. 6 is a graph showing the relationship between the relative intensity of light and a wavelength of ultraviolet rays passed through a filter; FIG. 7 is a graph showing the relationship between the ultraviolet radiation time and an out-put current; and FIG. 8 is a cross-sectional view showing a configuration of modified electrode portions.

As shown in FIG. 2, the apparatus 1 for measuring the hardness of the ultraviolet curing transformation agent comprises a light source device 2 comprising a lamp 3, an optical filter member 5 through which ultraviolet rays having a predetermined wavelength among beams emitted from the light source device 2 pass, and a condenser 6 located in the rear of the optical filter member 5, and a measuring device 7 provided underneath the condenser 6.

In the measuring device 7, the ultraviolet curing transformation agent 8 having the same properties as the one to be used in printing materials in the actual operation is applied to an insulator 11. The measuring device 7 comprises an electrode portion A having two electrodes 9 and 10 provided at both sides of the ultraviolet curing transformation agent 8 on the insulator 11, a lead wire connected to the electrodes 9 and 10, and a power supply 12 for supplying voltage, located at a predetermined position of the lead wire, and a current meter 13 (electric conductivity measuring instrument).

The transformation agent 8, especially a pigment as a stain will be described. It is preferable that the transformation agent 8 is applied to the insulator 11 to the same thickness as in the work in the actual operation. Further, it is preferable that the electrodes 9 and 10 are formed of metal electrodes. The voltage supplied from the power supply 12 may be direct current voltage or alternative current voltage. In FIG. 2, the condenser 6 is provided but if the intensity of light from the lamp 3 is large enough, the condenser may be omitted. Accordingly, the optical filter member 5 is placed between the light source device 2 and the ultraviolet curing transformation agent 8. Note that reference numeral 14 of FIG. 2 is a display and a memory.

As shown in FIG. 2, the optical filter member 5 removes the beams having a wavelength which cause the photoelectromotive force in the pigment, from the beams including ultraviolet rays emitted from the lamp 3 of the light source device 2 and the beams reflected from a reflector 4. Then, the ultraviolet rays having a predetermined wavelength are condensed by the condenser 6 and irradiate the ultraviolet curing transformation agent 8 in the measuring device 7.

In this condition, as shown in FIG. 3, the spectral absorption region of magenta is 450 nm to 600 nm and UV rays having 546 nm-, 577 nm- and 579 nm-wavelengths cause the photoelectromotive force as shown in FIG. 4. The yellow pigment has the spectral absorption region of 400 nm to 500 nm, and the cyan has the spectral absorption region of 600 nm to 700 nm. It should be noted that the absorption occurred below 450 nm in the spectral absorption region of magenta is not due to the pigment but monomer, polymer, or a starting material which does not cause the photoelectromotive force in the pigment (in the case of another pigment, the spectral absorption region of monomer, polymer and starting material does not cause the photoelectromotive force in the pigment).

On the other hand, the wavelength characteristic of UV rays emitted from the light source device 2 is in the range of 200 nm to 600 nm as shown in FIG. 4. The UV rays having the wavelength characteristic of FIG. 4 are transmitted through the optical filter member 5 having a transmissivity shown in FIG. 5, and then the UV rays have the characteristic shown in FIG. 6. In other words, 450 nm to 650 nm wavelengths which are in the UV ray absorption region of the cyan pigment are removed.

In a case that the UV curing transformation agent 8 is irradiated with the UV rays having a predetermined wavelength through the optical filter member 5, the time change in electric conductivity is measured. Then, as shown in FIG. 7, as the time elapses., the electric conductivity is decreased, so that the hardness of the UV curing transformation agent comprising pigment can be determined from the decrement of the electric conductivity. In FIG. 7, ○ denotes yellow pigment; 58 , cyan pigment; △, magenta pigment; and ●, black pigment.

As shown in FIG. 7, as predetermined seconds elapse, the electric conductivity is decreased, which shows the hardness of the UV curing transformation agent 8. The electric conductivity is varied in accordance with the thickness of the UV curing transformation agent 8 and the power of UV ray radiation; however, the printing process is properly carried out if the same condition as in the actual printing process is set.

For some kinds of printing materials, a plurality of colors need to be applied. In this case, back-wrapping phenomenon (the first color ink attaches over the second color ink), and crystallization (the transformation area of the second color ink is varied) may occur. However, the hardness to prevent the inferior printing can be derived from the predetermined electric conductivity.

Since each UV curing transformation agent 8 has the different concentration of components (pigment, monomer, olygomer) and the resistance of the yellow pigment is different from the magenta pigment, the UV ray radiation time (seconds) and the intensity of UV ray are set for each printing material.

The electrode portion A of the hardness measuring apparatus 1 may have the configuration shown in FIG. 8. That is, the UV curing transformation agent 18 comprising a stain is applied to one of the electrodes 19a and 19b. The electrodes 19a and 19b may be made of indium oxide (IO film), tin oxide (NESA film), or a film that tin oxide is doped to indium oxide (ITO film, conductive transparent glass), which transmits light including UV rays emitted from the light source (see FIG. 7), and the electrodes may be placed on the substrates 22a and 22b. In FIG. 8, there is a coating 23 capable of transmitting UV rays on the upper substrate 22b as an optical filter member for transmitting UV rays having a predetermined wavelength.

In FIG. 8, the lower electrode 19a has the same configuration as the upper electrode 19b, but the lower electrode 19a does not have to be made of the member having a light transmitting property. It may be made of metal. There is an insulator 21 between the electrodes 19a and 19b. The insulator 21 may be glass, rubber or others as long as it suitably insulates.

Alternatively, the UV curing transformation agent 18 containing a stain is applied all over the surface of one of the upper and lower electrodes 19a and 19b, and then the upper and lower electrodes are piled up. Accordingly, the transformation agent 18 is sandwiched between the electrodes 19a and 19b, which eliminates the insulator 21 because the electrodes 19a and 19b are not in contact each other. Further, in accordance with the electrode portion A described with FIG. 8, the optical filter member 5 and the condenser shown in FIG. 2 may be omitted. Furthermore, when the electrodes 19a and 19b sandwich the transformation agent 18, the transformation agent 18 may be set in the environment in which oxygen is shut off.

The electrodes of FIG. 2 may be arranged so as to be set in the environment in which oxygen is shut off. In other words, the electrode portion A is set in a predetermined gas atmosphere, e.g., containing a main component of nitrogen gas so that the electrode portion A is not in contact with oxygen and the UV ray having a specific wavelength is emitted. Further, in a case of immersing the electrode portion A into a solution to shut off oxygen, it is preferable to arrange the electrode portion A of FIG. 2 such that the insulator 11 is formed into a box shape and that the transformation agent 8 is applied to the upper surface of the insulator 11, and that solution is poured into the insulator 11.

Next, referring to FIG. 9A and FIG. 9B, the second embodiment of the present invention will be described.

Figure 9A:
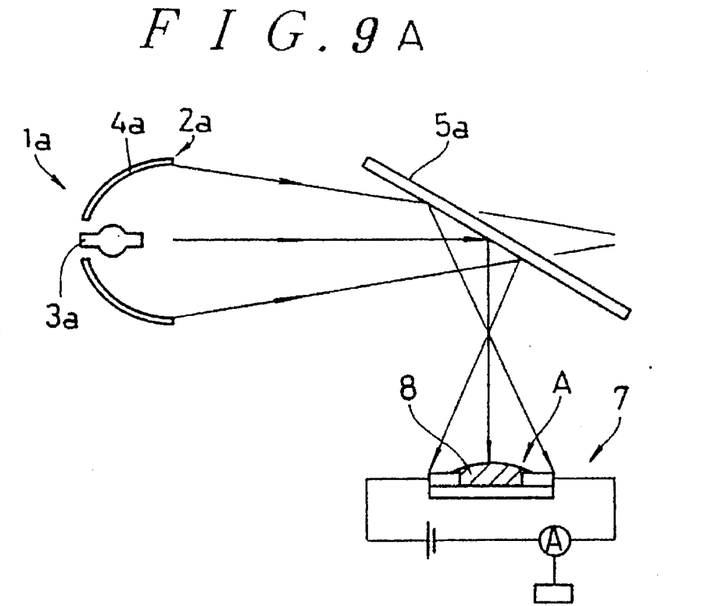
FIGS. 9A and 9B are schematic views showing a measuring apparatus according to the second embodiment of the present invention.
Figure 9B:
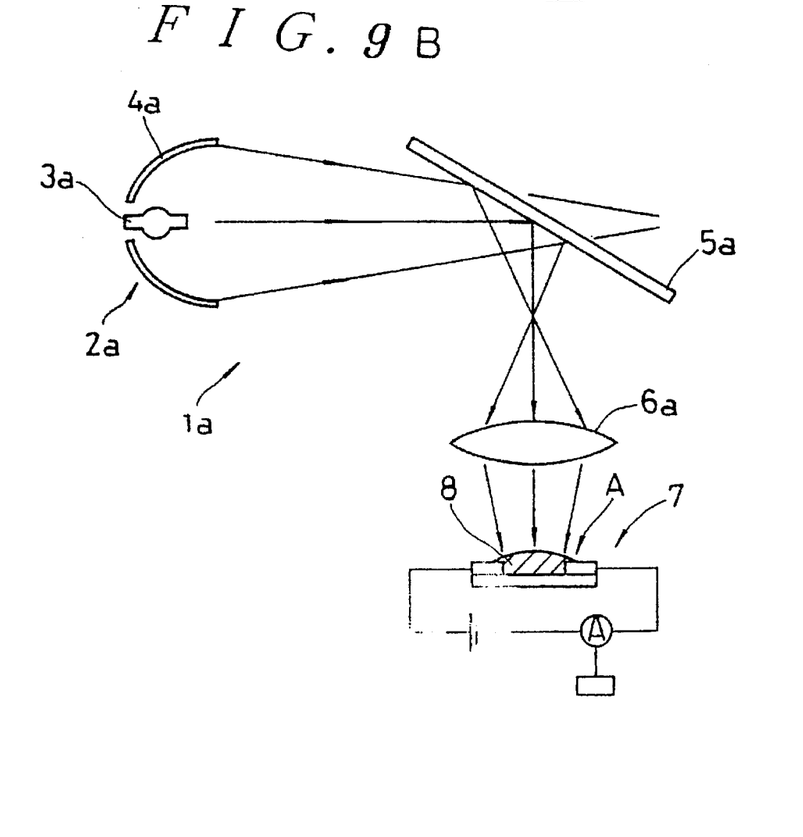

As shown in FIG. 9A, the apparatus 1a for measuring the hardness of the UV curing transformation agent comprises a light source device 2a which comprises a lamp 3a and a curved- or an elliptical reflector 4a, a cold mirror 5a capable of transmitting UV rays having a predetermined wavelength among beams including UV rays emitted from the light source device 2a, and a measuring device 7 provided at a location where the UV ray reflected from the cold mirror 5a irradiates. Note that the measuring device 7 has the same configuration as in the first embodiment.

Accordingly, with this configuration, the beams are emitted from the light source device 2a to the cold mirror 5a, and the cold mirror 5a reflects the UV rays having a predetermined wavelength and transmits the beams causing the photoelectromotive force in the pigment. Therefore, the photoelectromotive force is not generated in the UV curing transformation agent 8 applied in the measuring device 7 and its electric conductivity is properly measured. Then, the hardness of the agent is determined from the decrement of the electric conductivity. As shown in FIG. 9B, it is convenient to set a condenser 6a between the cold mirror 5a and the UV curing transformation agent 8 if necessary.

Next, the third embodiment of the present invention will be described with reference to FIG. 10.

Figure 10:
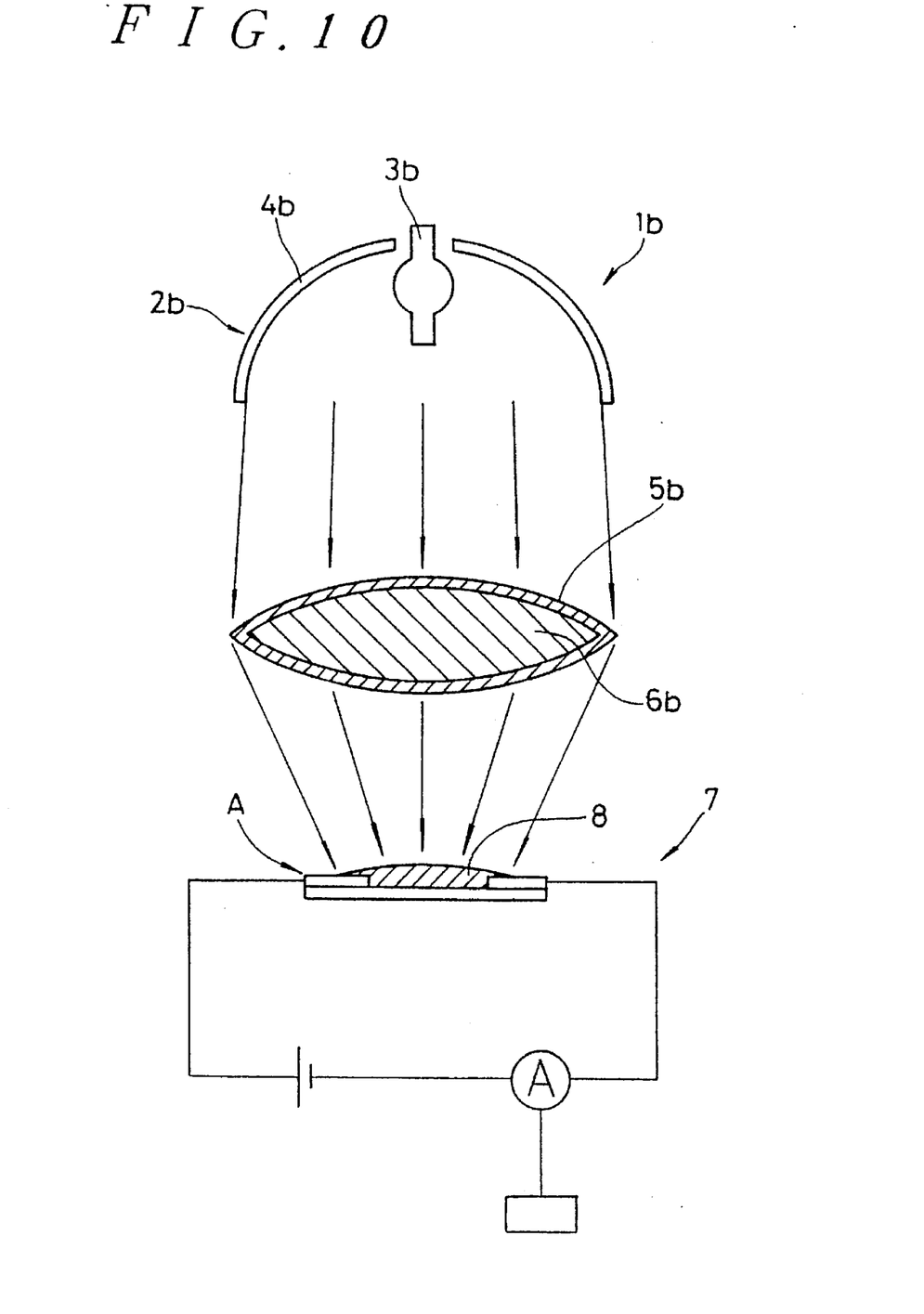
FIG. 10 is a schematic view showing a measuring apparatus according to the third embodiment of the present invention.

As shown in FIG. 10, the apparatus 1b for measuring the hardness of the UV curing transformation agent comprises a light source device 2b which comprises a lamp 3b and a curved-mirror 4b, a condenser 6b having an optical filter member 5b provided on the surface thereof, and a measuring device 7 provided at a location where the condensed beams from the condenser 6b irradiate. The measuring device 7 has the same configuration as in the first embodiment.

Accordingly, the UV rays having a wavelength causing the photoelectromotive force in the pigment is eliminated from the beams emitted from the light source device 2b while transmitted through the condenser 6b. Therefore, the hardness of the UV curing transformation agent 8 which is cured with UV rays passed through the condenser 6b is appropriately determined from the decrement of the electric conductivity.

Next, the fourth embodiment of the present invention will be described hereunder with reference to FIG. 11.

Figure 11:
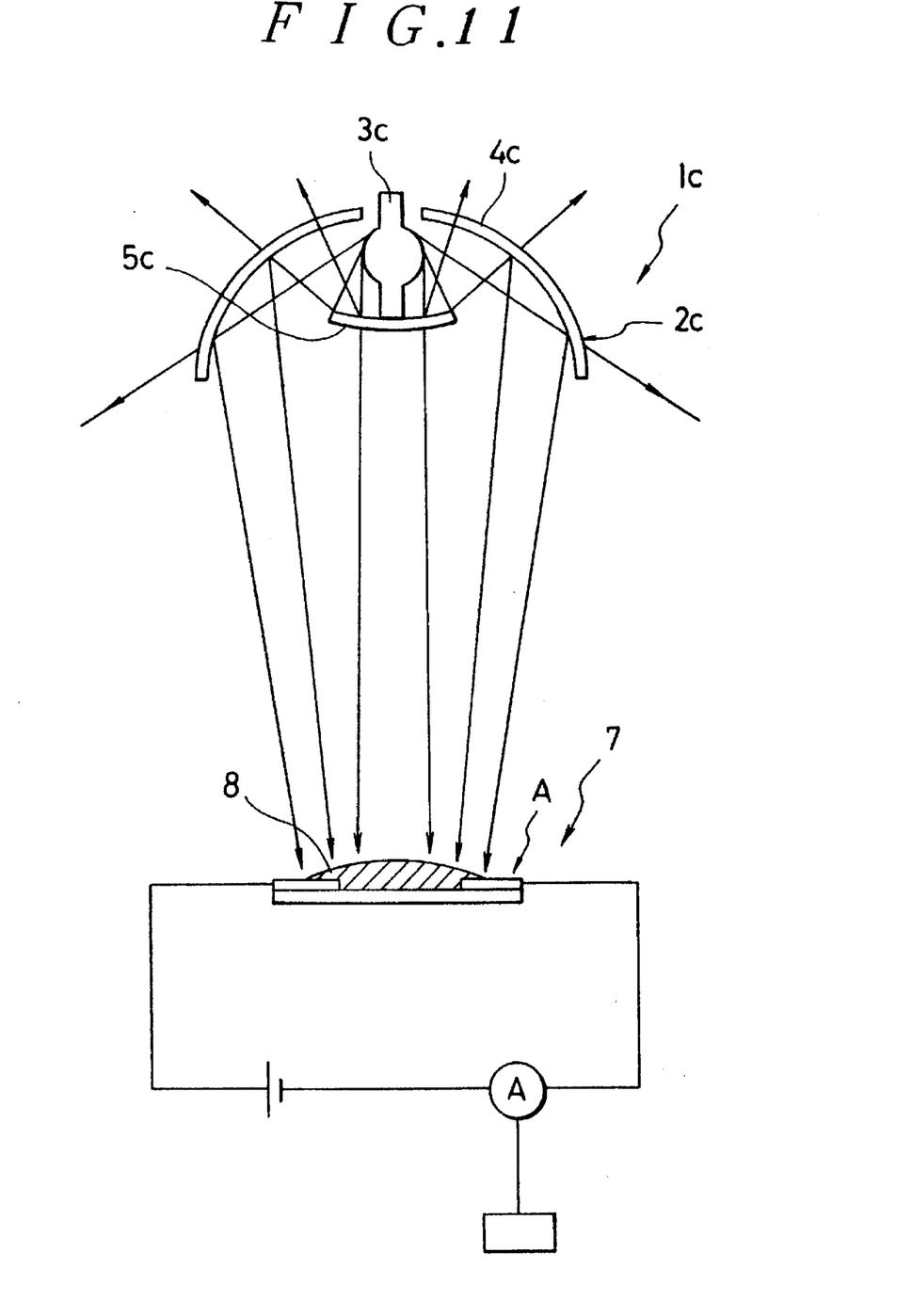
FIG. 11 is a schematic view showing a measuring apparatus according to the fourth embodiment of the present invention.

Referring to FIG. 11, the apparatus 1c for measuring the hardness of the UV curing transformation agent comprises a light source device 2c which comprises a lamp 3c and a reflector 4c, an optical filter member 5c provided at the end of the lamp 3c, and a measuring device 7 provided at a location where the ultraviolet ray from the light source device 2c irradiates. The reflector 4c comprises a cold mirror to reflect an ultraviolet ray having a predetermined wavelength. The optical filter member 5c transmits an ultraviolet ray having a predetermined wavelength and reflects other beams. Note that the measuring device 7 has the same configuration as in the first embodiment.

Accordingly, as the light traveling in straight among beams including ultraviolet rays emitted from the light source device 2c goes to the optical filter member 5c, only the ultraviolet rays having the predetermined wavelength irradiate the UV curing transformation agent 8 in the measuring device 7. Further, as light goes to the reflector 4c, the ultraviolet rays having the predetermined wavelength are reflected by the reflector 4c and light having another wavelengths passes through the reflector 4c.

Therefore, the photoelectromotive force is not generated in the pigment of the UV curing transformation agent 8, which enables the measurement of the hardness of the UV curing transformation agent 8 based on the decrement of the electric conductivity. The condenser may be provided in the optical path if necessary.

Thus, in each embodiment, the hardness of the UV curing transformation agent 8 can be determined by measuring the decrement of the electric conductivity of the UV curing transformation agent 8 in accordance with any application of the UV curing transformation agent 8. That is, in the case of the use of the monochromic UV curing transformation agent 8, the high hardness (dryness) is suitable, so that it is preferably that the saturation of the electric conductivity of the UV curing transformation agent 8 is measured.

Further, in the case of applying the UV curing transformation agents plural times, the appropriate dryness is assured by finding the electric conductivity so that the crystallization and the back-trapping do not occur after the first application, corresponding to the thickness of the agent and the color of the UV curing transformation agent.

Furthermore, when the optical filter member is made of dielectric multilayer films capable of transmitting (or reflecting) UV rays, or made of colored glass, the UV ray having a predetermined wavelength can be emitted to the UV curing transformation agent without causing the photoelectromotive force in the pigment, which enables the measurement of the electric conductivity.

It should be noted that the transformation agents include transformation agents to be directly or indirectly pressed to a work, using a printing plate such as a relief plate, an intaglio plate, a perforated plate and a flat plate, agents to be attached to a work, e.g., using a reverse coating or curtain coating, and adhesive agents forming a film on a work, e.g., using a spray method, a dipping method, a spinner method, a slurry method and an electronic drift method, for example, paint, ink, resist ink, adhesive, filler, putty, insulating material, barrier material, inductive paste and others.

The structure of every apparatus is simplified by using the electrodes in the second embodiment to the fourth embodiment shown in FIG. 8. Further, the hardness measuring apparatus shown in each embodiment can be used in the existing UV curing device and accurately dry the transformation agent on the printing material.

Thus, as described above, the present invention shows the following effects.

(1) Although the UV curing transformation agent contains a pigment, since the UV rays from which the UV rays in the spectral absorption region of the pigment causing the photoelectromotive force are removed irradiate the transformation agent, the hardness of the UV curing transformation agent can be determined by measuring the electric conductivity of the UV curing transformation agent. Accordingly, the appropriate curing process is carried out. Further, the condition of the hardness can be determined for any types of the UV curing transformation agent. Accordingly, the appropriate intensity of UV ray and the UV radiation time for the transformation agent on a printing material are accurately and rapidly determined. Furthermore, the measuring apparatus of the present invention can be utilized in the existing UV ray irradiation device.

(2) In the electrode portion, the upper and lower electrodes sandwich the UV curing transformation agent containing a stain to shut off air, and the UV rays having the predetermined wavelength are emitted, so that this condition is the same as in the case of treating an anaerobic material. Accordingly, the hardness of the transformation agent can accurately be determined. Further, when the electrode portion is placed in a gas atmosphere in which oxygen is shut off, the condition is also the same as in the case of the anaerobic material, so that the hardness of the transformation agent can accurately be determined.

(3) The optical filter material is placed at the reflector. Then, the UV rays having the predetermined wavelength among the UV rays emitted from the light source device are reflected by the reflector and irradiate the UV curing transformation agent. Accordingly, the pigment of the UV curing transformation agent is cured without causing the photoelectromotive force even though the UV rays irradiate. Therefore, the hardness of the UV curing transformation agent can be determined by measuring the electric conductivity of the transformation agent. Moreover, this is superior in heat treatment by UV radiation and in prevention of deterioration of the measuring apparatus due to heat.

(4) In the optical filter member, the condenser is provided in the optical path of the light from the light source device, and the optical filter member is placed at the surface of the condenser. As the UV rays go to the condenser, the UV rays having the predetermined wavelength are transmitted through it and irradiate the UV curing transformation agent. Accordingly, the electric conductivity can be measured without the generation of photoelectromotive force in the pigment of the transformation agent, which enables the measurement of the hardness (dryness) of the UV curing transformation agent, and which simplifies the structure of the apparatus.

(5) Since the optical filter member is pieced at the distal end of the lamp as a cold mirror, the UV rays having the predetermined wavelength among the UV rays emitted from the light source device irradiate the UV curing transformation agent, and the electric conductivity can be measured without the generation of the photoelectromotive force in the pigment of the UV curing transformation agent. Accordingly, the hardness of the transformation agent can be determined based on the decrement of the electric conductivity. Moreover, although the light source device is close to the object to be measured, this measuring apparatus ban be utilized.

(6) The condenser is provided in the optical path between the optical filter member and the UV curing transformation agent, so that the quantity of UV rays which is decreased while the UV rays pass through the optical filter member is compensated. Therefore, the measurement time is shortened and also the curing time is shortened.

(7) Since the optical filter member comprises the conductive multilayer coherent film, the UV rays having the predetermined wavelength are reflected or transmitted to irradiate the UV curing transformation agent, depending upon the location of the optical filter member.

(8) After the UV rays in the spectral absorption region which causes the photoelectromotive force in the UV curing transformation agent are removed, the UV rays irradiate the transformation agent, and the electric conductivity is measured by the measuring device placed on the side of the UV curing transformation agent. Accordingly, the intensity of UV rays and the UV radiation time are accurately determined to cure the transformation agent. Further, if the condenser is utilized when the UV rays having the predetermined wavelength irradiate, the UV radiation time is shortened.

(9) The condition of the hardness of the UV curing transformation agent is determined based on the decrement of the electric conductivity of the transformation agent. Therefore, the appropriate hardness of the transformation agent is assured in accordance with the condition of the UV curing transformation agent, e.g., a monochromic agent or a multicolored agent.

What is claimed is:

1. An apparatus for measuring hardness of an ultraviolet curing transformation agent comprising a stain comprising:

a light source device for emitting beams including ultraviolet rays;

an optical filter member through which the ultraviolet rays having a predetermined wavelength among the beams emitted from said light source device pass; and a measuring device for measuring electric conductivity of said ultraviolet curing transformation agent comprising the stain, provided at a location where the ultraviolet rays having the predetermined wavelength irradiate, said measuring device comprising an electrode portion including electrodes on which said ultraviolet curing transformation agent is applied;

said electrodes being connected through a power supply and a measuring device for measuring the electric conductivity.

2. An apparatus for measuring hardness of an ultraviolet curing transformation agent comprising a stain according to claim 1, wherein said ultraviolet curing transformation agent is applied to one of said electrodes and said electrodes are piled up; and one of said electrodes to be irradiated with the ultraviolet rays from said light source device is made of member capable of transmitting light.

3. An apparatus for measuring hardness of an ultraviolet curing transformation agent comprising a stain according to claim 1, said electrode portion is provided in a predetermined gas atmosphere in which oxygen is shut off.

4. An apparatus for measuring hardness of an ultraviolet curing transformation agent comprising a stain according to claim 1, wherein said optical filter member is provided at a reflector placed in an optical path of light emitted from said light source device, and the ultraviolet rays having the predetermined wavelength are reflected to said ultraviolet curing transformation agent in said measuring apparatus.

5. An apparatus for measuring hardness of an ultraviolet curing transformation agent comprising a stain according to claim 1, wherein said optical filter member is provided at a condenser placed in an optical path of light emitted from said light source device, and the ultraviolet rays having the predetermined wavelength irradiate said ultraviolet curing transformation agent in said measuring apparatus.

6. An apparatus for measuring hardness of an ultraviolet curing transformation agent comprising a stain according to claim 1, wherein said light source device comprises a lamp and a reflector; and said optical filter member is flat and provided at an end of said lamp of said light source device so as to interrupt an optical path of light emitted from Said lamp and said optical filter member is capable of transmitting the ultraviolet rays having the predetermined wavelength to irradiate said ultraviolet curing transformation agent; and said reflector of said light source device reflects the ultraviolet rays having the predetermined wavelength among the beams emitted from said lamp to irradiate said ultraviolet curing transformation agent.

7. An apparatus for measuring hardness of an ultraviolet curing transformation agent comprising a stain according to claim 1, wherein a condenser is provided at an optical path of light emitted from said light source device between the location of said optical filter member and said ultraviolet curing transformation agent.

8. An apparatus for measuring hardness of an ultraviolet curing transformation agent comprising a stain according to claim 1, wherein said optical filter member is a coherent filter of conductive multilayer films which removes light in the spectral absorption region of said stain of said ultraviolet curing transformation agent.

9. A method for measuring hardness of an ultraviolet curing transformation agent comprising a stain comprising:

a first step of irradiating an ultraviolet curing transformation agent with light from which light in the spectral absorption region of said stain of said ultraviolet curing transformation agent is removed; and a second step of measuring electric conductivity of said ultraviolet curing transformation agent.

10. A method for measuring hardness of an ultraviolet curing transformation agent comprising a stain according to claim 9, wherein said first step is a step of removing light in the spectral absorption region of said stain of said ultraviolet curing transformation agent by said optical filter member, condensing ultraviolet rays and irradiating said ultraviolet curing transformation agent with said ultraviolet rays.

11. A method for measuring hardness of an ultraviolet curing transformation agent comprising a stain according to claim 9, wherein said second step is a step of determining the hardness based on the decrement of the electric conductivity.

12. A method for measuring hardness of an ultraviolet curing transformation agent comprising a stain comprising:

a first step of irradiating an ultraviolet curing transformation agent with light from which light in the spectral absorption region of said stain of said ultraviolet curing transformation agent is removed by an optical filter member; and a second step of providing said ultraviolet curing transformation agent in a predetermined gas atmosphere in which oxygen is shut off, and measuring electric conductivity of said ultraviolet curing transformation agent.

13. A method for measuring hardness of an ultraviolet curing transformation agent comprising a stain according to claim 12, wherein said first step is a step of removing light in the spectral absorption region of said stain of said ultraviolet curing transformation agent by said optical filter member, condensing ultraviolet rays and irradiating said ultraviolet curing transformation agent with said ultraviolet rays.

14. A method for measuring hardness of an ultraviolet curing transformation agent comprising a stain according to claim 12, wherein said second step is a step of determining the hardness based on the decrement of the electric conductivity.

* * * * *